United States Patent [19]

Sullivan et al.

[11] Patent Number: 5,728,568

[45] Date of Patent: Mar. 17, 1998

[54] HUMAN GDP-MANNOSE 4,6 DEHYDRATASE

[75] Inventors: Francis Sullivan, Belmont; Ronald Kriz, Hudson; Ravindra Kumar, Belmont, all of Mass.

[73] Assignee: Genetics Institute, Inc., Cambridge, Mass.

[21] Appl. No.: 753,233

[22] Filed: Nov. 22, 1996

[51] Int. Cl.$^6$ .............. C12N 1/21; C12N 9/88; C12N 15/60; C12N 15/63

[52] U.S. Cl. .............. 435/232; 435/320.1; 435/325; 435/254.11; 435/252.3; 536/23.2

[58] Field of Search ................ 435/69.1, 232, 435/325, 320.1, 147; 536/23.2

[56] References Cited

FOREIGN PATENT DOCUMENTS

WO95/30001  11/1995  WIPO .

OTHER PUBLICATIONS

Kaufman et al., Nucleic Acids Res. 19, 4485–4490 (1991).
R. Kaufman, Methods in Enzymology 185, 537–566 (1990).
Yamamoto et al., Archives of Biochemistry and Biophysics 300:694–698 (1993).
Kornfled et al., Biochimica et Biophysica Acta 117:79–87 (1966).
Fujiwara et al (1995) Database DDBJ, accession D61843.
Genbank accession nos. U42580, U17055, U32570 (1996).
Li et al (1995) Virol.212:134–150 "Analysis of 43kb of the Chlorella Virus PBCV–1 330–kbgenome. Map Positions 45 to 88' ".

*Primary Examiner*—Eric Grimes
*Attorney, Agent, or Firm*—Scott A. Brown; Thomas J. DesRosier

[57] ABSTRACT

The invention provides a novel GDP-mannose 4,6-dehydratase.

7 Claims, No Drawings

HUMAN GDP-MANNOSE 4,6 DEHYDRATASE

The present invention relates to the cloning and isolation of a human GDP-mannose 4,6 dehydratase, which is useful (among other purposes) for the manufacture of complex carbohydrates and as a target for screening of small molecule antagonists of activity of the enzyme.

BACKGROUND OF THE INVENTION

Complex carbohydrate moieties play an important role in many ligand/receptor binding events. For example, P-selectin ligand (see WO95/30001) found on the surface of neutrophils contains sialyl Lewis x ($sLe_x$) moieties which are essential to binding of the ligand to its receptor, P-selectin, on the surface of vascular endothelium. The interaction of P-selectin ligand and P-selectin is involved in the development of inflammatory responses, including both those which produce desired immune responses and those which cause disease states. As a result, many complex carbohydrate moieties, including $sLe_x$, are currently under investigation for use as therapeutics to interfere with detrimental ligand/receptor binding events.

Complex carbohydrates are usually synthesized with the aid of enzymes which can convert more easily obtainable starting materials and intermediates into necessary moieties which are more difficult to produce by non-enzymatic chemical synthesis. For example, $sLe_x$ contains an essential fucose moiety which can be added enzymatically starting with GDP-fucose, which is readily obtained from GDP-mannose using the appropriate enzymes. As a result, the identification and isolation of a wide variety of enzymes for such purpose has been a continuing goal for those interested in carbohydrate production. In particular, the identification of enzymes capable of converting GDP-mannose to GDP-fucose has been sought to aid in the development of production methods for $sLe_x$ and other fucose-containing carbohydrates.

One route of synthesis which is used in the production of fucose-containing carbohydrates is through the conversion of GDP-mannose to GDP-fucose, which can then be used to incorporate the fucose moiety into the synthetic product. This conversion involves multiple steps, each of which can be catalyzed by an appropriate enzyme. The first step in this process is the conversion of GDP-mannose to GDP-4-keto-6-deoxy-mannose. In vivo this conversion is made by the action of an GDP-mannose 4,6-dehydratase.

A GDP-mannose dehydratase enzyme has been cloned and isolated from *E. coli* (GenBank accession number U38473). However, the enzymes from different species may have different in vivo and in vitro characteristics and activities, both beneficial and detrimental, which may affect their relative usefulness for production of complex carbohydrates. Nevertheless, no human dehydratase enzyme has yet been identified.

Certain disease states have also been associated with defects in the action of such dehydratases. For example, the human disease leukocyte adhesion deficiency II (LADII) may be due to a defect in the dehydratase enzyme. The correlation of other dehydratase enzymes with disease states will allow the examination of therapies for such conditions.

Since these dehydratase enzymes are also responsible for the in vivo production of fucose-containing carbohydrate moieties, blocking their activity through the use of antagonists or other means can provide another route for interruption of unwanted inflammatory responses and other conditions dependent upon the production of fucose-containing carbohydrate moieties. Isolated dehydratases can be used as a target to screen for inhibitors of enzyme activity which can be used for this purpose.

Therefore, it would be desirable to identify, clone and isolate additional dehydratase enzymes to expand the panoply of enzymes available to the carbohydrate synthetist. It would also be desirable to identify additional dehydratase which are associated with certain disease states to allow the examination and development of treatments for such conditions. It would also be desirable to identify and isolate additional human dehydratase enzymes which can serve as targets for screening inhibitors.

SUMMARY OF THE INVENTION

In certain embodiments, the present invention provides an isolated polynucleotide comprising a nucleotide sequence selected from the group consisting of:

(a) the nucleotide sequence of SEQ ID NO:1;

(b) a nucleotide sequence encoding the amino acid sequence of SEQ ID NO:2;

(c) a nucleotide sequence encoding the amino acid sequence of SEQ ID NO:3;

(d) a nucleotide sequence encoding a fragment of the amino acid sequence of (b) or (c) having GM4,6D activity;

(e) a nucleotide sequence capable of hybridizing with the sequence of (a) which encodes a peptide having GM4,6D activity; and (f) allelic variants of the sequence of (a), (b) or (c). Preferably, the nucleotide sequence comprises the nucleotide sequence of SEQ ID NO:1, a nucleotide sequence encoding the amino acid sequence of SEQ ID NO:2, or a nucleotide sequence encoding the amino acid sequence of SEQ ID NO:3. Expression vectors comprising such polynucleotide and an expression control sequence and host cells transformed with such vectors are also provided.

Other embodiments provide for a process for producing a GM4,6D, said process comprising:

(a) establishing a culture of the host cell of the present invention in a suitable culture medium; and (b) isolating said enzyme from said culture (including without limitation from conditioned media, cell lysate or inclusion bodies). Compositions comprising a peptide made according to such processes are also provided.

Compositions comprising peptides encoded by polynucleotides of the present invention are also provided.

In yet further embodiments, the present invention provides compositions comprising a peptide comprising an amino acid sequence selected from the group consisting of:

(a) the amino acid sequence of SEQ ID NO:2;

(b) the amino acid sequence of SEQ ID NO:3; and (c) a fragment of the amino acid sequence of (a) or (b) having GM4,6D activity;

said peptide being substantially free from association with other proteins. Preferably, the peptide comprises the amino acid sequence of SEQ ID NO:2 or SEQ ID NO:3. Pharmaceutical compositions comprising such peptides and a pharmaceutically acceptable carrier are also provided.

Other embodiments of the present invention provide for a method for identifying an inhibitor of GM4,6D activity, said method comprising:

(a) combining a substrate, a candidate inhibitor compound, and a composition comprising a GM4,6D peptide; and (b) observing whether said GM4,6D peptide converts said substrate.

Inhibitors according to such methods and pharmaceutical compositions incorporating them are also provided.

The invention also provides compositions comprising an antibody which binds to the peptide of the present invention.

Methods are also provided for treating or ameliorating diseases affected by the level of cellular fucosylation or diseases affected by the fucosylation of glycoconjugates. Such methods of treatment comprise administering a pharmaceutical composition comprising an inhibitor of GM4,6P activity to a mammalian subject.

DETAILED DESCRIPTION OF THE INVENTION

Applicants have cloned and isolated a novel human GDP-mannose 4,6-dehydratase (hereinafter "GM4,6D").

A cDNA encoding the GM4,6D of the present invention was isolated as described in Example 1. The sequence of the cDNA is reported as SEQ ID NO: 1. Two predicted amino acid sequence encoded by such cDNA are reported as SEQ ID NO:2 and SEQ ID NO:3. The invention also encompasses allelic variations of the cDNA sequence as set forth in SEQ ID NO: 1, that is, naturally-occurring alternative forms of the cDNA of SEQ ID NO: 1 which also encode enzymes of the present invention.

A cDNA clone ("P-38-1") encoding the GM4,6D enzyme of the invention was deposited with the American Type Culture Collection on Nov. 15, 1996 as accession number ATCC 98260.

The human enzyme GDP-mannose 4,6-dehydratase (GM4,6D) converts GDP-mannose to GDP-4-keto-6-deoxy-mannose as the first step in the conversion of GDP-mannose to GDP-fucose. As used herein, "GM4,6D activity" means the ability to convert GDP-mannose to GDP-4-keto-6-deoxy-mannose, including without limitation such activity as measured by the assays described in Example 2 below or similar assays.

The polynucleotides of the present invention could be used to produce protein for the manufacture of GDP-fucose from GDP-mannose and for the identification of inhibitors of the enzyme's activity. GDP-fucose would be useful in the production of fucosylated glycoconjugates such as sialyl lewis X and its derivatives. Inhibitors of the enzyme would be useful in treating human conditions where fucose play a role such as inflammation and inflammatory disorders, arthritis, transplant rejection, asthma, sepsis, reperfusion injury, stroke, infection, reproduction and development.

Polynucleotides encoding GM4,6D would also be useful in developing an assay for defects in the enzyme, such as potentially might occur in Leukocyte deficiency type II, LADII. The polynucleotides could be used in gene replacement therapy. The gene sequence could also be used to modify cell line to increase the amounts of GDP-fucose that they make, for use in production of recombinant proteins.

Also included in the invention are isolated DNAs which hybridize to the DNA sequence set forth in SEQ ID NO: 1 under stringent (e.g. 4×SSC at 65° C. or 50% formamide and 4×SSC at 42° C.), or relaxed (4×SSC at 50 C. or 30–40% formamide at 42° C.) conditions.

The isolated polynucleotides of the invention may be operably linked to an expression control sequence such as the pMT2 or pED expression vectors disclosed in Kaufman et at., Nucleic Acids Res. 19, 4485–4490 (1991), in order to produce the GM4,6D peptides recombinantly. Many suitable expression control sequences are known in the art. General methods of expressing recombinant proteins are also known and are exemplified in R. Kaufman, Methods in Enzymology 185,537–566 (1990). As defined herein "operably linked" means enzymatically or chemically ligated to form a covalent bond between the isolated polynucleotide of the invention and the expression control sequence, in such a way that the GM4,6D peptide is expressed by a host cell which has been transformed (transfected) with the ligated polynucleotide/expression control sequence.

A number of types of cells may act as suitable host cells for expression of the GM4,6D peptide. Suitable host cells are capable of attaching carbohydrate side chains characteristic of functional GM4,6D peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The GM4,6D peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), incorporated herein by reference.

Alternatively, it may be possible to produce the GM4,6D peptide in lower eukaryotes such as yeast, fungi or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. Suitable fungi strains include Aspergillus sp. or any fungi strain capable of expressing heterologous proteins.

The GM4,6D peptide of the invention may also be expressed as a product of transgenic animals, e.g., as a component of the milk of transgenic cows, goats, pigs, or sheep which are characterized by somatic or germ cells containing a polynucleotide encoding the GM4,6D peptide.

The GM4,6D peptide of the invention may be prepared by culturing transformed host cells under culture conditions necessary to express a GM4,6D peptide of the present invention. The resulting expressed protein may then be purified from culture medium or cell extracts as described in the examples below.

Alternatively, the GM4,6D peptide of the invention is concentrated using a commercially available protein concentration filter, for example, an Amicon or Millipore Pellicon ultrafiltration unit. Following the concentration step, the concentrate can be applied to a purification matrix such as a gel filtration medium.

Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the GM4,6D peptide from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the GM4,6D peptide. Some or all of the foregoing purification steps, in various combinations, can also be employed to provide a substantially homogeneous isolated recombinant protein. The GM4,6D peptide thus purified is substantially free of other mammalian or other host cell proteins and is defined in accordance with the present invention as "isolated GM4,6D peptide".

The GM4,6D of the present invention may be used to screen unknown compounds having inhibitory activity for the dehydratase and, by derivation, inhibitory activity for conditions affected by overexpression or other undesirable level of activity of such enzyme. Many assays for dehydratase activity are known and may be used with enzyme of the present invention to screen unknown compounds. For example, such assays include those described in Example 2. These assays may be performed manually or may be automated or robotized for faster screening. Methods of automation and robotization are known to those skilled in the art.

In one possible screening assay, a first mixture is formed by combining a GM4,6D peptide of the present invention with GDP-mannose by such peptide, and the amount of conversion in the first mixture ($B_0$) is measured. A second mixture is also formed by combining the peptide, the substrate and the compound or agent to be screened, and the amount of conversion in the second mixture (B) is measured. The amounts of conversion in the first and second mixtures are compared, for example, by performing a $B/B_0$ calculation. A compound or agent is considered to be capable of inhibiting enzyme activity if a decrease in conversion in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the GM4,6D of the present invention are in the development of monoclonal and polyclonal antibodies. Such antibodies may be generated by employing purified forms of the enzyme or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study enzyme activity and disease states related to such enzyme.

Pharmaceutical compositions containing inhibitors (e.g., anti-inflammatory agents) identified by the screening method of the present invention may be employed to treat, for example, diseases affected by the level of cellular fucosylation or the fucosylation of glycoconjugates including, protein, lipids and glycosaminoglycans. Pharmaceutical compositions of the invention comprise a therapeutically effective amount of such an inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 µg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration may be intravenous, but other known methods of administration for inhibitory and anti-inflammatory agents may be used. Administration of the inhibitory compounds identified by the method of the invention can be carried out in a variety of conventional ways. For example, for topical administration, the inhibitor compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the inhibitor compound, about 2 to about 5% W/W of a gelling agent. The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B.F. Goodrich), hydroxypropyl methylcellulose phthalates such as Methocel (K100M premium; Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mM phosphate buffer, pH 7.5.

Cutaneous or subcutaneous injection may also be employed and in that case the inhibitor compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the inhibitor compound of the invention will be in the form of pyrogen-free, parenterally acceptable aqueous solutions. A preferred pharmaceutical composition for intravenous injection should contain, in addition to the inhibitor compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

The amount of inhibitor compound in the pharmaceutical composition of the present invention will depend upon the nature and severity of the condition being treated, and on the nature of prior treatments which the patient has undergone. Ultimately, the attending physician will decide the amount of inhibitor compound with which to treat each individual patient.

Inhibitor compounds identified using the method of the present invention may be administered alone or in combination with other anti-inflammation agents and therapies.

EXAMPLE 1

Cloning of cDNA for GM4,6D

HL-60 cDNA Library Construction

A cDNA library was constructed from HL-60 cells as described in US patent WO95/30001. This is a plasmid based cDNA library, constructed as 38 separate pools each, representing 30,000 to 50,000 individual clones.

Clone Identification

The 38 library pools were combined in pairs to produce a total of 19 pools. 100 ng of DNA was taken from each pool and used as template for a polymerase chain reaction using the following two GDP mannose dehydratase deoxyribonucleotides:

5'-TGATGAGCCAGAGGACTTTGTCATAGCTAC-3' (SEQ ID NO:4)

5'-CAGAAAGTCCACTTCAGTCGGTCGGTAGTA-3' (SEQ ID NO:5)

The reaction conditions were set up as recommended by the manufacturer of Taq polymerase (Perkin Elmer) and the cycle conditions were as follows: 94° 1 min, 68° 3 min. Repeat for 30 cycles.

At the end of the reaction, an aliquot is taken and examined by agarose gel to determine the pools containing the dehydratase gene. The reaction done on combined pools (29 and 30) as well as (37 and 38) gave the expected 200 bp fragment. These pools were then examined separately and the positive pools were determined to be pool #30 and #38. The 200 bp PCR product was agarose gel purified and an aliquot was used for a subsequent reamplification and purification to further purify the fragment away from nonspecific products. This purified fragment was then random primer labeled with $^{32}p$ following standard protocols, and was used as probe to identify GDP-MD clones. A total of ~150,000 colonies from each pool were plated on $LB_{amp100}$, the colonies were transferred to nitrocellulose and hybridized to probe using stringent hybridization conditions. Positive colonies were subjected to one round of colony purification, and individual positive clones were purified and confirmed by DNA sequence determination.

EXAMPLE 2

Enzyme Activity Assays

Assays of dehydratase include, without limitation, incubation of radiolabeled ($^{14}C$ or $^3H$) on unlabeled GDP-mannose in the presence of salts, buffers and cofactors with enzyme or enzyme extracts, and separation of the reactants and products by HPLC (for example, as described in Yamamoto et al. (1993) Archives of Biochemistry and Biophysics, vol. 300, 694–698). Alternatively, dehydratase activity can be assayed by coupling the reaction with the enzyme(s) GDP-4-keto-6-deoxy-mannose, epimerase, reductae and monitoring the coupled oxidation of NADPH using, for example, visible or fluorescent spectroscopy (for example, as described in Yamamoto et al., supra). In another alternative, dehydratase activity can be monitored by following the absorbance of the product GDP-4-keto-6-deoxy-mannose at 325 nm in alkali solution (for example, as described by Kornfled and Ginsberg (1966) Biochimica et Biophysica Acta, vol. 117, 79–87).

What is claimed is:

1. An isolated polynucleotide comprising a nucleotide sequence selected from the group consisting of:
   (a) the nucleotide sequence of SEQ ID NO:1;
   (b) a nucleotide sequence encoding the amino acid sequence of SEQ ID NO:2;
   (c) a nucleotide sequence encoding the amino acid sequence of SEQ ID NO:3;
   (d) a nucleotide sequence encoding a fragment of the amino acid sequence of (b) or (c) having GDP-mannose, 4,6 dehydratase (GM 4,6D) activity;
   (e) a nucleotide sequence which encodes a peptide having GM4,6D activity and which hybridizes with the sequence of (a) in either 4×SSC at 65° C. or 50% formamide and 4×SSC at 42° C., and
   (f) allelic variants of the nucleotide sequence of SEQ ID NO:1.

2. The polynucleotide of claim 1 comprising the nucleotide sequence of SEQ ID NO:1.

3. The polynucleotide of claim 1 comprising a nucleotide sequence encoding the amino acid sequence of SEQ ID NO:2.

4. The polynucleotide of claim 1 comprising a nucleotide sequence encoding the amino acid sequence of SEQ ID NO:3.

5. An expression vector comprising the polynucleotide of claim 1 and an expression control sequence.

6. A host cell transformed with the vector of claim 5.

7. A process for producing a GM4,6D, said process comprising:
   (a) establishing a culture of the host cell of claim 6 in a suitable culture medium; and
   (b) isolating said enzyme from said culture.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 1521 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:1:

```
GCCGCGTTCC  TGCCGGCACC  GCGCCTGCCC  TCTGCCGCGC  TCCGCCCTGC  CGCCGACCGC    60
```

```
ACGCCCGCCG CGGGACATGG CACACGCACC GGCACGCTGC CCCAGCGCCC GGGGCTCCGG      120

GGACGGCGAG ATGGGCAAGC CCAGGAACGT GGCGCTCATC ACCGGTATCA CAGGCCAGGA      180

TGGTTCCTAC CTGGCTGAGT TCCTGCTGGA GAAAGGCTAT GAGGTCCATG GAATTGTACG      240

GCGGTCCAGT TCATTTAATA CGGGTCGAAT TGAGCATCTG TATAAGAATC CCCAGGCTCA      300

CATTGAAGGA AACATGAAGT TGCACTATGG CGATCTCACT GACAGTACCT GCCTTGTGAA      360

GATCATTAAT GAAGTAAAGC CCACAGAGAT CTACAACCTT GGAGCCCAGA GCCACGTCAA      420

AATTTCCTTT GACCTCGCTG AGTACACTGC GGACGTTGAC GGAGTTGGCA CTCTACGACT      480

TCTAGATGCA GTTAAGACTT GTGGCCTTAT CAACTCTGTG AAGTTCTACC AAGCCTCAAC      540

AAGTGAACTT TATGGGAAAG TGCAGGAAAT ACCCCAGAAG GAGACCACCC CTTTCTATCC      600

CCGGTCACCC TATGGGGCAG CAAAACTCTA TGCCTATTGG ATTGTGGTGA ACTTCCGTGA      660

GGCGTATAAT CTCTTTGCAG TGAACGGCAT TCTCTTCAAT CATGAGAGTC CCAGAAGAGG      720

AGCTAATTTC GTTACTCGAA AAATTAGCCG GTCAGTAGCT AAGATTTACC TTGGACAACT      780

GGAATGTTTC AGTTTGGGAA ATCTGGATGC CAAACGAGAT GGGGCCATG CCAAGGACTA       840

TGTGGAGGCT ATGTGGTTGA TGTTGCAGAA TGATGAGCCG GAGGACTTCG TTATAGCTAC      900

TGGGGAGGTC CATAGTGTCC GGAATTTGT CGAGAAATCA TTCTTGCACA TTGGAAAAAC       960

CATTGTGTGG GAAGGAAAGA ATGAAAATGA AGTGGGCAGA TGTAAAGAGA CCGGCAAAGT     1020

TCACGTGACT GTGGATCTCA AGTACTACCG GCCAACTGAA GTGGACTTTC TGCAGGGCGA     1080

CTGCACCAAA GCGAAACAGA AGCTGAACTG GAAGCCCGG GTCGCTTTCG ATGAGCTGGT      1140

GAGGGAGATG GTGCACGCCG ACGTGGAGCT CATGAGGACA AACCCCAATG CCTGAGCAGC     1200

GCCTCGGAGC CCGGCCCGCC CTCCGGCTAC AATCCCGCA GAGTCTCCGG TGCAGACGCG      1260

CTGCGGGGAT GGGGAGCGGC GTGCCAATCT GCGGGTCCCC TGCGGCCCCT GCTGCCGCTG     1320

CGCTGTCCCG GCCGCAAGAG CGGGGCCGCC CCGCCGAGGT TTGTAGCAGC CGGGATGTGA     1380

CCCTCCAGGG TTTGGGTCGC TTTGCGTTTG TCGAAGCCTC CTCTGAATGG CTTTGTGAAA     1440

TCAAGATGTT TTAATCACAT TCACTTTACT TGAAATTATG TTGTTACACA ACAAATTGTG     1500

GGGCCTTCAA ATTGTTTTTC C                                              1521
```

( 2 ) INFORMATION FOR SEQ ID NO:2:

( i ) SEQUENCE CHARACTERISTICS:
        ( A ) LENGTH: 354 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:2:

```
Met Gly Lys Pro Arg Asn Val Ala Leu Ile Thr Gly Ile Thr Gly Gln
 1               5                  10                  15

Asp Gly Ser Tyr Leu Ala Glu Phe Leu Leu Glu Lys Gly Tyr Glu Val
            20                  25                  30

His Gly Ile Val Arg Arg Ser Ser Ser Phe Asn Thr Gly Arg Ile Glu
        35                  40                  45

His Leu Tyr Lys Asn Pro Gln Ala His Ile Glu Gly Asn Met Lys Leu
    50                  55                  60

His Tyr Gly Asp Leu Thr Asp Ser Thr Cys Leu Val Lys Ile Ile Asn
65                  70                  75                  80

Glu Val Lys Pro Thr Glu Ile Tyr Asn Leu Gly Ala Gln Ser His Val
```

|     |     |     |     | 85  |     |     |     | 90  |     |     |     | 95  |     |     |
|-----|-----|-----|-----|-----|-----|-----|-----|-----|-----|-----|-----|-----|-----|-----|
| Lys | Ile | Ser | Phe | Asp | Leu | Ala | Glu | Tyr | Thr | Ala | Asp | Val | Asp | Gly | Val |
|     |     |     | 100 |     |     |     |     | 105 |     |     |     | 110 |     |     |
| Gly | Thr | Leu | Arg | Leu | Leu | Asp | Ala | Val | Lys | Thr | Cys | Gly | Leu | Ile | Asn |
|     |     | 115 |     |     |     |     | 120 |     |     |     | 125 |     |     |     |
| Ser | Val | Lys | Phe | Tyr | Gln | Ala | Ser | Thr | Ser | Glu | Leu | Tyr | Gly | Lys | Val |
|     | 130 |     |     |     |     | 135 |     |     |     | 140 |     |     |     |     |
| Gln | Glu | Ile | Pro | Gln | Lys | Glu | Thr | Thr | Pro | Phe | Tyr | Pro | Arg | Ser | Pro |
| 145 |     |     |     |     | 150 |     |     |     |     | 155 |     |     |     |     | 160 |
| Tyr | Gly | Ala | Ala | Lys | Leu | Tyr | Ala | Tyr | Trp | Ile | Val | Val | Asn | Phe | Arg |
|     |     |     |     | 165 |     |     |     | 170 |     |     |     |     | 175 |     |     |
| Glu | Ala | Tyr | Asn | Leu | Phe | Ala | Val | Asn | Gly | Ile | Leu | Phe | Asn | His | Glu |
|     |     |     | 180 |     |     |     |     | 185 |     |     |     | 190 |     |     |     |
| Ser | Pro | Arg | Arg | Gly | Ala | Asn | Phe | Val | Thr | Arg | Lys | Ile | Ser | Arg | Ser |
|     |     | 195 |     |     |     |     | 200 |     |     |     | 205 |     |     |     |     |
| Val | Ala | Lys | Ile | Tyr | Leu | Gly | Gln | Leu | Glu | Cys | Phe | Ser | Leu | Gly | Asn |
|     | 210 |     |     |     |     | 215 |     |     |     | 220 |     |     |     |     |     |
| Leu | Asp | Ala | Lys | Arg | Asp | Trp | Gly | His | Ala | Lys | Asp | Tyr | Val | Glu | Ala |
| 225 |     |     |     |     | 230 |     |     |     |     | 235 |     |     |     |     | 240 |
| Met | Trp | Leu | Met | Leu | Gln | Asn | Asp | Glu | Pro | Glu | Asp | Phe | Val | Ile | Ala |
|     |     |     |     | 245 |     |     |     |     | 250 |     |     |     |     | 255 |     |
| Thr | Gly | Glu | Val | His | Ser | Val | Arg | Glu | Phe | Val | Glu | Lys | Ser | Phe | Leu |
|     |     |     | 260 |     |     |     |     | 265 |     |     |     | 270 |     |     |     |
| His | Ile | Gly | Lys | Thr | Ile | Val | Trp | Glu | Gly | Lys | Asn | Glu | Asn | Glu | Val |
|     |     | 275 |     |     |     |     | 280 |     |     |     | 285 |     |     |     |     |
| Gly | Arg | Cys | Lys | Glu | Thr | Gly | Lys | Val | His | Val | Thr | Val | Asp | Leu | Lys |
|     | 290 |     |     |     |     | 295 |     |     |     | 300 |     |     |     |     |     |
| Tyr | Tyr | Arg | Pro | Thr | Glu | Val | Asp | Phe | Leu | Gln | Gly | Asp | Cys | Thr | Lys |
| 305 |     |     |     | 310 |     |     |     |     | 315 |     |     |     |     |     | 320 |
| Ala | Lys | Gln | Lys | Leu | Asn | Trp | Lys | Pro | Arg | Val | Ala | Phe | Asp | Glu | Leu |
|     |     |     |     | 325 |     |     |     |     | 330 |     |     |     |     | 335 |     |
| Val | Arg | Glu | Met | Val | His | Ala | Asp | Val | Glu | Leu | Met | Arg | Thr | Asn | Pro |
|     |     |     | 340 |     |     |     |     | 345 |     |     |     | 350 |     |     |     |
| Asn | Ala |

( 2 ) INFORMATION FOR SEQ ID NO:3:

( i ) SEQUENCE CHARACTERISTICS:
        ( A ) LENGTH: 372 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:3:

| Met | Ala | His | Ala | Pro | Ala | Arg | Cys | Pro | Ser | Ala | Arg | Gly | Ser | Gly | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Glu | Met | Gly | Lys | Pro | Arg | Asn | Val | Ala | Leu | Ile | Thr | Gly | Ile | Thr |
|     |     |     | 20  |     |     |     |     | 25  |     |     |     | 30  |     |     |     |
| Gly | Gln | Asp | Gly | Ser | Tyr | Leu | Ala | Glu | Phe | Leu | Leu | Glu | Lys | Gly | Tyr |
|     |     | 35  |     |     |     |     | 40  |     |     |     | 45  |     |     |     |     |
| Glu | Val | His | Gly | Ile | Val | Arg | Arg | Ser | Ser | Ser | Phe | Asn | Thr | Gly | Arg |
|     | 50  |     |     |     |     | 55  |     |     |     | 60  |     |     |     |     |     |
| Ile | Glu | His | Leu | Tyr | Lys | Asn | Pro | Gln | Ala | His | Ile | Glu | Gly | Asn | Met |
| 65  |     |     |     | 70  |     |     |     |     | 75  |     |     |     |     |     | 80  |

| | | | | | | | | | | | | | | |
|---|---|---|---|---|---|---|---|---|---|---|---|---|---|---|
|Lys|Leu|His|Tyr|Gly<br>85|Asp|Leu|Thr|Asp|Ser<br>90|Thr|Cys|Leu|Val|Lys<br>95|Ile|
|Ile|Asn|Glu|Val<br>100|Lys|Pro|Thr|Glu|Ile<br>105|Tyr|Asn|Leu|Gly|Ala<br>110|Gln|Ser|
|His|Val|Lys<br>115|Ile|Ser|Phe|Asp|Leu<br>120|Ala|Glu|Tyr|Thr|Ala<br>125|Asp|Val|Asp|
|Gly|Val<br>130|Gly|Thr|Leu|Arg|Leu<br>135|Leu|Asp|Ala|Val|Lys<br>140|Thr|Cys|Gly|Leu|
|Ile<br>145|Asn|Ser|Val|Lys|Phe<br>150|Tyr|Gln|Ala|Ser|Thr<br>155|Ser|Glu|Leu|Tyr|Gly<br>160|
|Lys|Val|Gln|Glu|Ile<br>165|Pro|Gln|Lys|Glu|Thr<br>170|Thr|Pro|Phe|Tyr|Pro<br>175|Arg|
|Ser|Pro|Tyr|Gly<br>180|Ala|Ala|Lys|Leu|Tyr<br>185|Ala|Tyr|Trp|Ile|Val<br>190|Val|Asn|
|Phe|Arg|Glu<br>195|Ala|Tyr|Asn|Leu|Phe<br>200|Ala|Val|Asn|Gly|Ile<br>205|Leu|Phe|Asn|
|His|Glu<br>210|Ser|Pro|Arg|Arg|Gly<br>215|Ala|Asn|Phe|Val|Thr<br>220|Arg|Lys|Ile|Ser|
|Arg<br>225|Ser|Val|Ala|Lys|Ile<br>230|Tyr|Leu|Gly|Gln|Leu<br>235|Glu|Cys|Phe|Ser|Leu<br>240|
|Gly|Asn|Leu|Asp|Ala<br>245|Lys|Arg|Asp|Trp|Gly<br>250|His|Ala|Lys|Asp|Tyr<br>255|Val|
|Glu|Ala|Met|Trp<br>260|Leu|Met|Leu|Gln|Asn<br>265|Asp|Glu|Pro|Glu|Asp<br>270|Phe|Val|
|Ile|Ala|Thr<br>275|Gly|Glu|Val|His|Ser<br>280|Val|Arg|Glu|Phe|Val<br>285|Glu|Lys|Ser|
|Phe|Leu<br>290|His|Ile|Gly|Lys|Thr<br>295|Ile|Val|Trp|Glu|Gly<br>300|Lys|Asn|Glu|Asn|
|Glu|Val<br>305|Gly|Arg|Cys|Lys|Glu<br>310|Thr|Gly|Lys|Val|His<br>315|Val|Thr|Val|Asp<br>320|
|Leu|Lys|Tyr|Tyr|Arg<br>325|Pro|Thr|Glu|Val|Asp<br>330|Phe|Leu|Gln|Gly|Asp<br>335|Cys|
|Thr|Lys|Ala|Lys<br>340|Gln|Lys|Leu|Asn|Trp<br>345|Lys|Pro|Arg|Val|Ala<br>350|Phe|Asp|
|Glu|Leu|Val<br>355|Arg|Glu|Met|Val|His<br>360|Ala|Asp|Val|Glu|Leu<br>365|Met|Arg|Thr|
|Asn|Pro|Asn<br>370|Ala| | | | | | | | | | | | |

( 2 ) INFORMATION FOR SEQ ID NO:4:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:4:

TGATGAGCCA GAGGACTTTG TCATAGCTAC    30

( 2 ) INFORMATION FOR SEQ ID NO:5:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:5:

CAGAAAGTCC ACTTCAGTCG GTCGGTAGTA 30